United States Patent
Mirtsching et al.

(10) Patent No.: US 7,613,330 B2
(45) Date of Patent: *Nov. 3, 2009

(54) METHODS AND SYSTEMS FOR TRACKING AND MANAGING LIVESTOCK THROUGH THE PRODUCTION PROCESS

(75) Inventors: Warren Mirtsching, Fort Collins, CO (US); John Felix, Berthoud, CO (US); Mark A. Gustafson, Windsor, CO (US)

(73) Assignee: JBS Swift & Company, Greeley, CO (US)

( * ) Notice: Subject to any disclaimer, the term of this patent is extended or adjusted under 35 U.S.C. 154(b) by 75 days.

This patent is subject to a terminal disclaimer.

(21) Appl. No.: 11/695,712

(22) Filed: Apr. 3, 2007

(65) Prior Publication Data

US 2007/0260347 A1   Nov. 8, 2007

Related U.S. Application Data

(60) Provisional application No. 60/789,013, filed on Apr. 3, 2006.

(51) Int. Cl.
*G06K 9/00* (2006.01)
(52) U.S. Cl. .................................... 382/110
(58) Field of Classification Search ................. 382/110; 452/155; 426/392
See application file for complete search history.

(56) References Cited

U.S. PATENT DOCUMENTS

| | | | |
|---|---|---|---|
| 337,334 A | 3/1886 | Jones et al. |
| 1,485,755 A | 3/1924 | Alcock |
| 1,900,573 A | 3/1933 | McArthur |
| 2,544,681 A | 3/1951 | Harsham et al. |
| 2,544,724 A | 3/1951 | Rentschler |
| 2,621,362 A | 10/1952 | Cosden |
| 2,870,018 A | 1/1959 | Person et al. |
| 2,879,539 A | 3/1959 | Cervin |
| 2,979,411 A | 4/1961 | Pircon |
| 3,314,103 A | 4/1967 | Rains |
| 3,537,130 A | 11/1970 | McDonnell |
| 3,626,550 A | 12/1971 | Troy |
| 3,657,770 A | 4/1972 | Wallace |

(Continued)

FOREIGN PATENT DOCUMENTS

AU    2003272338 A1    3/2004

(Continued)

OTHER PUBLICATIONS

Boleman, National Beef Quality Audit—1995: Survey of Producer-Related Defects and Carcass Quality and Quantity Attributes, J. Anim. Sci. 76:96-103 (1998).

(Continued)

*Primary Examiner*—Phuoc Tran
(74) *Attorney, Agent, or Firm*—Sheridan Ross P.C.

(57) ABSTRACT

Systems and methods are described that provide a relatively quick and easy way of tracing meat products to their origins. Specifically, methods of tracing a fully processed meat product back through the production process use windows of traceability to quickly identify which lots were being processed at a particular time. Identification and cross-referencing during the production process also allow for further tracking of the origin of meat products, ultimately up to their feedlot of origin.

14 Claims, 7 Drawing Sheets

U.S. PATENT DOCUMENTS

| | | |
|---|---|---|
| 3,736,622 A | 6/1973 | Wali |
| 3,863,294 A | 2/1975 | Barbee |
| 4,023,574 A | 5/1977 | Nemec |
| 4,221,021 A | 9/1980 | Swilley |
| 4,307,490 A | 12/1981 | Watkins et al. |
| 4,340,993 A | 7/1982 | Cook |
| 4,358,872 A | 11/1982 | VanZandt |
| 4,495,676 A | 1/1985 | Hartmetz |
| 4,561,149 A | 12/1985 | Nijhuis |
| 4,675,947 A | 6/1987 | Clatfelter et al. |
| 4,733,971 A | 3/1988 | Pratt |
| 4,774,741 A | 10/1988 | Bernharadt et al. |
| 4,815,042 A | 3/1989 | Pratt |
| 4,827,727 A | 5/1989 | Caracciola |
| 4,860,403 A | 8/1989 | Webb et al. |
| 4,889,433 A | 12/1989 | Pratt |
| 4,910,024 A | 3/1990 | Pratt |
| 4,931,933 A | 6/1990 | Chen et al. |
| 5,007,336 A | 4/1991 | Bernhardt et al. |
| 5,008,821 A | 4/1991 | Pratt et al. |
| 5,167,569 A | 12/1992 | Davis |
| 5,219,244 A | 6/1993 | Skeels |
| 5,282,940 A | 2/1994 | Griffis et al. |
| 5,315,505 A | 5/1994 | Pratt et al. |
| 5,340,211 A | 8/1994 | Pratt |
| RE34,776 E | 11/1994 | Pratt |
| 5,369,032 A | 11/1994 | Pratt |
| 5,401,501 A | 3/1995 | Pratt |
| 5,478,990 A * | 12/1995 | Montanari et al. .......... 235/375 |
| 5,486,145 A | 1/1996 | Dorsthorst et al. |
| 5,512,014 A | 4/1996 | Burnett |
| 5,529,793 A | 6/1996 | Garner et al. |
| 5,534,271 A | 7/1996 | Ware et al. |
| 5,573,002 A | 11/1996 | Pratt |
| 5,595,066 A | 1/1997 | Zwanikken et al. |
| 5,668,634 A | 9/1997 | Newman |
| 5,673,647 A | 10/1997 | Pratt |
| 5,704,830 A | 1/1998 | Van Ochten |
| 5,803,906 A | 9/1998 | Pratt et al. |
| 5,836,880 A | 11/1998 | Pratt |
| 5,855,507 A | 1/1999 | Fisher et al. |
| 5,879,732 A | 3/1999 | Caracciolo, Jr. et al. |
| 5,888,132 A | 3/1999 | Burnett |
| 5,899,802 A | 5/1999 | Burnett |
| 5,958,714 A | 9/1999 | Gordon et al. |
| 6,000,361 A | 12/1999 | Pratt |
| 6,001,655 A | 12/1999 | Spadaro et al. |
| 6,019,674 A | 2/2000 | Austin |
| 6,084,407 A | 7/2000 | Ellis |
| 6,104,966 A | 8/2000 | Haagensen |
| 6,120,367 A | 9/2000 | Scott et al. |
| 6,131,744 A | 10/2000 | Pratt |
| 6,135,055 A | 10/2000 | Pratt |
| 6,159,090 A | 12/2000 | Thompson |
| 6,190,250 B1 | 2/2001 | Volk et al. |
| 6,198,834 B1 * | 3/2001 | Belk et al. ................. 382/110 |
| 6,200,210 B1 | 3/2001 | Pratt |
| 6,231,435 B1 | 5/2001 | Pilger |
| RE37,266 E | 7/2001 | Te Dorsthorst et al. |
| 6,290,592 B1 | 9/2001 | Allen et al. |
| 6,318,289 B1 | 11/2001 | Pratt |
| 6,322,436 B2 | 11/2001 | Potter et al. |
| 6,342,839 B1 | 1/2002 | Curkendall |
| 6,364,759 B2 | 4/2002 | Allen et al. |
| 6,458,024 B1 | 10/2002 | Potter et al. |
| 6,478,667 B2 | 11/2002 | Bell et al. |
| 6,516,746 B2 | 2/2003 | Pratt |
| 6,519,954 B1 | 2/2003 | Prien et al. |
| 6,546,304 B2 | 4/2003 | Thorvaldsson et al. |
| 6,547,726 B2 | 4/2003 | Pratt et al. |
| 6,579,236 B2 | 6/2003 | Pratt |
| 6,592,517 B2 | 7/2003 | Pratt et al. |
| 6,712,685 B2 | 3/2004 | Potter et al. |
| 6,724,309 B2 | 4/2004 | Grose et al. |
| 6,736,272 B2 | 5/2004 | Pratt |
| 6,796,892 B2 | 9/2004 | Allen et al. |
| 6,859,672 B2 | 2/2005 | Roberts et al. |
| 6,891,961 B2 | 5/2005 | Eger et al. |
| 6,896,607 B2 | 5/2005 | Potter et al. |
| 6,912,434 B2 | 6/2005 | van den Nieuwelaar et al. |
| 6,975,223 B1 | 12/2005 | Mladen et al. |
| 6,975,233 B2 | 12/2005 | Grose et al. |
| 7,022,005 B2 | 4/2006 | Potter et al. |
| 7,063,836 B2 | 6/2006 | Garner et al. |
| 7,400,256 B2 | 7/2008 | Knopik et al. |
| 7,440,901 B1 | 10/2008 | Dlott et al. |
| 2001/0031617 A1 | 10/2001 | Allen et al. |
| 2001/0034201 A1 | 10/2001 | Bell et al. |
| 2002/0077055 A1 | 6/2002 | Allen et al. |
| 2002/0182999 A1 | 12/2002 | Bell et al. |
| 2003/0154729 A1 | 8/2003 | Prien et al. |
| 2003/0190879 A1 | 10/2003 | Bell et al. |
| 2003/0198724 A1 | 10/2003 | Schaefer et al. |
| 2004/0026920 A1 | 2/2004 | Meischen |
| 2004/0115322 A1 | 6/2004 | Osborn |
| 2005/0042980 A1 | 2/2005 | Allen et al. |
| 2005/0049518 A1 | 3/2005 | Nel |
| 2005/0051109 A1 | 3/2005 | Fantin et al. |
| 2005/0142997 A1 | 6/2005 | Richards |
| 2005/0181720 A1 | 8/2005 | Osborn |
| 2005/0186896 A1 | 8/2005 | Nielsen |
| 2005/0221746 A1 | 10/2005 | Bell et al. |
| 2005/0272057 A1 | 12/2005 | Abrahamsen et al. |
| 2005/0284380 A1 | 12/2005 | Montgomery |
| 2006/0041408 A1 | 2/2006 | McGoogan et al. |
| 2006/0041412 A1 | 2/2006 | Engelke et al. |
| 2006/0041413 A1 | 2/2006 | Burghardi et al. |
| 2006/0041419 A1 | 2/2006 | Newcombe et al. |
| 2007/0258625 A1 | 11/2007 | Mirtsching |

FOREIGN PATENT DOCUMENTS

| | | |
|---|---|---|
| AU | 760810 | 12/2005 |
| CA | 2372042 | 11/2000 |
| CA | 2497726 A1 | 3/2004 |
| EP | 0090478 | 10/1983 |
| EP | 0353199 | 1/1990 |
| EP | 1175151 | 8/2005 |
| FR | 2495438 | 6/1982 |
| FR | 2519846 | 7/1983 |
| GB | 1478258 | 6/1977 |
| GB | 2147791 | 5/1985 |
| JP | 8009876 | 1/1996 |
| JP | 8023869 | 1/1996 |
| SU | 0833182 | 5/1981 |
| SU | 1009382 | 4/1983 |
| SU | 1391566 | 4/1988 |
| WO | WO8101641 | 6/1981 |
| WO | WO9819550 | 5/1998 |
| WO | WO0154509 | 8/2001 |
| WO | WO0195716 | 12/2001 |
| WO | WO0247485 | 6/2002 |
| WO | WO02058474 | 8/2002 |
| WO | WO2004021782 A2 | 3/2004 |
| WO | WO2004085997 | 10/2004 |
| WO | WO2005099466 | 10/2005 |

OTHER PUBLICATIONS

Bosilevac, Development and Evaluation of an On-Line Hide Decontamination Procedure for Use in a Commercial Beef Processing Plant, Journal of Food Protection, vol. 68, No. 2, 2005, pp. 265-272.

Clare, Improving Tenderness of Normal and Callipyge Lambs with Calcium Chloride, J. Anim. Sci. 75:377-385 (1997).

Cross, Influence of Breed, Sex, Age and Electrical Stimulation on Carcass and Palatability Traits of Three Bovine Muscles, Journal of Animal Science, vol. 58, No. 6, 1984, pp. 1358-1365.

Crouse, The Effect of Carcass Electrical Stimulation on Meat Obtained From Bos Indicus and Bos Taurus Cattle, Journal of Food Quality, 10, 1987, pp. 407-416.

Davey, Carcass Electrical Stimulation to Prevent Cold Shortening Toughness in Beef, Refrigeration Science and Technology, 1977, pp. 293-298.

Ducastaing, Effects of Electrical Stimulation on Post-mortem Changes in the Activities of Two Ca Dependent Neutral Proteinases and their Inhibitor in Beef Muscle, Meat Science 15, 1985, pp. 193-202.

Eikelenboom, The Effect of High and Low Voltage Electrical Stimulation on Beef Quality, Meat Science 15, 1985, pp. 247-254.

Eilers, Modification of Early-Postmortem Muscle pH and Use of Postmortem Aging to Improve Beef Tenderness, J. Anim. Sci., 74:790-798 (1996).

Epley, Meat Tenderness, retrieved from website http://www.extension.umn.edu/distribution/nutrition/DJ0856 on Apr. 4, 2006, 8 pages.

Fabiansson, The Influence of Low Voltage Electrical Stimulation on Some Physical and Sensoric Properties of Beef, Acta Agric Scand, 34:368-376 (1984).

Federal Register, Cooling and Chilling Requirements for Raw Meat and Poultry, vol. 61, No. 144, p. 38856 (Jul. 25, 1996).

Ferguson, Meat Standards Australia, A 'PACCP' Based Beef Grading Scheme for Consumers, 3) PACCP Requirements that Apply to Carcass Processing, 45th International Congress of Meat Science and Technology, Yokohama, Japan, 45:18-19 (1999).

Hildrum, Combined Effects of Chilling Rate, Low Voltage Electrical Stimulation and Freezing on Sensory Properties of Bovine *M. Longissimus dorsi*, Meat Science 52, 1999, pp. 1-7.

Kerth, Electrical Stimulation Effects on Tenderness of Five Muscles from Hampshire x Rambouillet Crossbred Lambs with the Callipyge Phenotype, J. Anim. Sci., 77:2951-2955 (1999).

McKeith, Tenderness Improvement of the Major Muscles of the Beef Carcass by Electric Stimulation, Journal of Food Science, vol. 46, 1981, pp. 1774-1776.

McNeal, Effects of Stunning and Decapitation on Broiler Activity During Bleeding, Blood Loss, Carcass, and Breast Meat Quality, Poultry Science 82:163-168 (2003).

Mies, Effects of Postmortem Aging on Beef Tenderness and Aging Guidelines to Maximize Tenderness of Different Beef Subprimal cuts, Program in Meat Science, Department of Animal Studies, Colorado State University, pp. 127-133.

Miller, Bovine *Longissimus dorsi* Muscle Glycogen and Color Response as Affected by Dietary Regimen and Post-Mortem Electrical Stimulation in Young Bulls, Meat Science 19, 1987, pp. 253-263.

Morgan, National Beef Tenderness Survey, J. Anim. Sci. 69:3274-3283 (1991).

Northcutt, Reference Guide for Solving Poultry Processing Problems, Bulletin 1156, May 1997, The University of Georgia College of Agricultural and Environmental Sciences, 6 pages.

Purchas, Effects of Growth Potential and Growth Path on Tenderness of Beef *Longissimus* Muscle From Bulls and Steers, J. Anim. Sci. 80:3211-3221 (2002).

Roeber, Effects of a Unique Application of Electrical Stimulation on Tenderness, Color, and Quality Attributes of the Beef *Longissimus* Muscle, J. Anim. Sci., 78:1504-1509 (2000).

Savell, Effect of Electrical Stimulation on Palatability of Beef, Lamb and Goat Meat, Journal of Food Science, vol. 42, No. 3, 1977, pp. 702-706.

Savell, A Research Note: Influence of Electrical Stimulation on Certain Characteristics of Heavy-Weight Beef Carcasses, 3 pages.

Stiffler, Electrical Stimulation Purpose, Application, and Results, Bulletin, Texas Agricultural Extension Service, 1982, pp. 1-8.

Takahashi, Effects of Low-Frequency Electrical Stimulation on Beef Tenderness, Meat Science 11, 1984, pp. 207-225.

Tatum, New Approaches for Improving Tenderness, Quality, and Consistency of Beef, Proceedings of the American Society of Animal Science, 1999, 10 pages.

Westervelt, Relationship Among Spinal Cord Severing, Electrical Stimulation and Postmortem Quality Characteristics of the Porcine Carcass, Journal of Animal Science, vol. 46, No. 5, 1978, pp. 1206-1211.

"US traceback system debate", available at http://www.ellinghuysen.com/news/articles/26845.shtml, printed Jan. 6, 2006, pp. 1-2.

"Beef Traceability Case Study", GS1 Ireland, Feb. 2005, 24 pages.

MICOTIL 300—Section 1—Chemical Product and Company, Elanco, effective date Feb. 8, 2006, pp. 1-9.

Pulmotil Medicated Premix—Section 1—Chemical Product and Company, Elanco, effective date Nov. 18, 2003, pp. 1-9.

"Environmental Assessment—INAD 9087—Zilpaterol Hydrochloride Type A Medicated Article (Premix) in Confinement Cattle", Sponsor Intervet Inc., Nov. 2001, pp. 1-14.

Optaflexx 45—Ractopamine Hydrochloride, Elanco, Apr. 11, 2004, pp. 1-2.

"What is Bovamine?", Nutrition Physiology Corporation, available at http://www.bovamine.com/products.html, printed Feb. 7, 2007, 2 pages.

Wines "Pig Organs Tainted With a Banned Steroid Sicken 70 in China", MY Times, Feb. 24, 2009, 2 pages.

International Search Report for International (PCT) Patent Application No. PCT/US07/08472, mailed Sep. 30, 2008.

Written Opinion for International (PCT) Patent Application No. PCT/US07/08472, mailed Sep. 30, 2008.

International Preliminary Report on Patentability for International (PCT) Patent Application No. PCT/US07/08472, mailed Dec. 11, 2008.

* cited by examiner

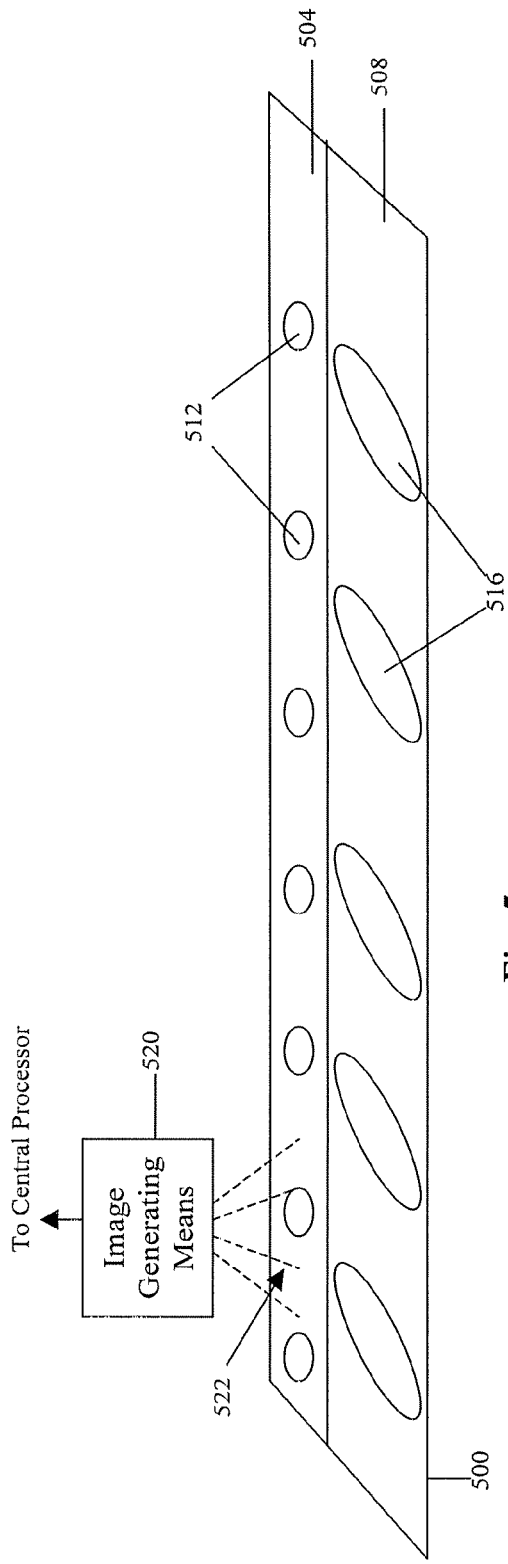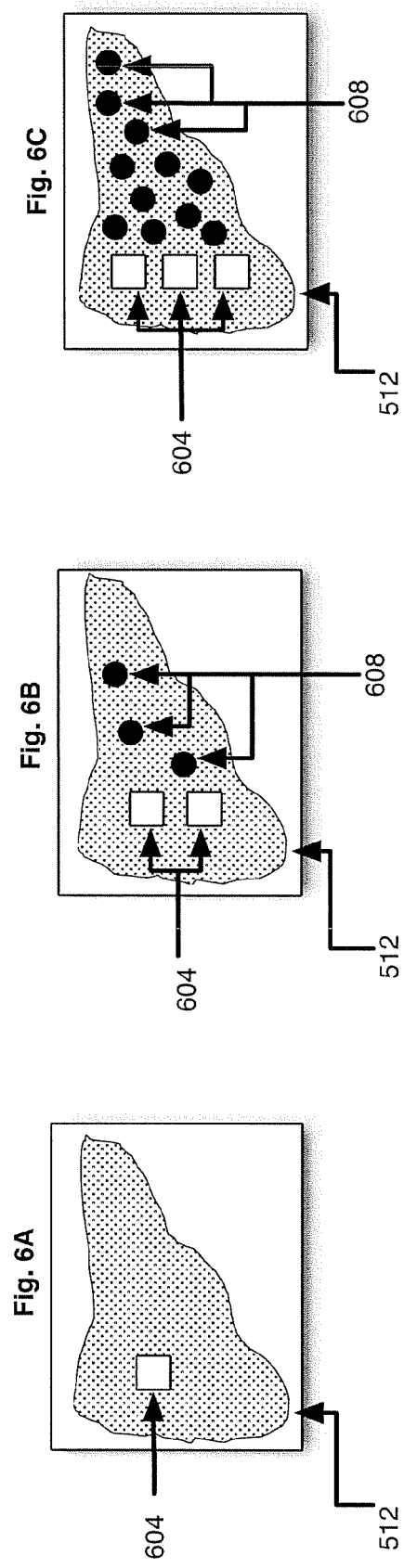

METHODS AND SYSTEMS FOR TRACKING AND MANAGING LIVESTOCK THROUGH THE PRODUCTION PROCESS

CROSS REFERENCE TO RELATED APPLICATIONS

The present application claims the benefits of U.S. Provisional Application Ser. No. 60/789,013 filed on Apr. 3, 2006, entitled "Method and System for Tracking and Managing Livestock Through the Production Process," which is incorporated herein in its entirety by this reference.

FIELD

The present invention generally relates to methods and systems for tracking livestock through the production process. More specifically, embodiments of the present invention provide for a relatively simple and quick way of tracing the origins of meat products.

BACKGROUND

During commercial meat production, a beef carcass is subjected to a number of different procedures. The animal is first slaughtered, the hide is removed from the carcass, and the carcass is washed. The carcass may then be contacted with hot water and/or steamed pasteurized, and the carcass may also be subjected to one or more electrical stimulation processes. During commercial meat production, the carcass may be attached to a trolley or shackle at different points in the meat processing line. The carcass then travels along the meat processing line where it is subjected to a number of processes, including those identified above, as well as weighing of the carcass and removal of various portions of the carcass. The carcasses are also inspected at a number of locations along the meat processing line, where certain information regarding carcasses may be collected and recorded by the inspectors and others.

During commercial meat production, it is common to track and identify meat carcasses while they are on the meat production line. Carcasses are tracked for a variety of reasons, including monitoring the efficiency of the meat production facility and to identify and monitor carcasses to ensure that meat has been safely handled and processed. In addition, carcasses may be tracked during meat production so that certain information may be accumulated and maintained while the carcass is in the meat production facility. This information may include the weight of the carcass, the specific type of animal from which the carcass was derived, data about the source of the animal (e.g., breeder, ranch location, etc.), and a variety of other information that may be used to track the carcass. This information may be used for a variety of purposes, including ensuring the meat has been properly aged, aiding and sorting carcasses before they are broken down into meat products for packaging, and tracking carcass information back to the producer of the animal or tracing carcass information from the farm to the packaged meat. In addition, information about carcasses that impact the price of meat, such as quality and cutability, may be collected at different locations in the plant.

Meat producers have therefore instituted tracking systems in meat processing plants. A unique identifier for each carcass that enters the meat processing line is used such that the carcass may be tracked and it can be verified that each carcass has been subjected to each procedure on the meat processing line (e.g., steam pasteurization, washing, trimming, electrical stimulation, and so on).

Furthermore, in response to mad cow disease outbreaks, the United States Government has been pushing for a "trace back" system that allows for a final meat product to be traced back to its lot of origin. Under this initiative, 169,000 producers have volunteered to receive a premises ID number, unique to the lot or origin of an animal. The USDA hopes to begin to issue ID numbers for animals within each lot. Timetables call for tracking of livestock shipments to begin as early as 2009. The idea of having a unique identification number for each lot and then for each animal produced within a given lot provides a way of tracing back any meat product to its origin. However, such a system has several fallbacks. Namely, the management of a database that contains unique identification members for every lot and then maintaining identification numbers for every animal within each lot can become computationally expensive. Furthermore, the management of such a system may become monetarily expensive as people are required to maintain and operate such a database. Another problem with the proposed idea is that in order for such a system to work each animal's identification number must be maintained and registered along at each step in the process. Therefore, redundant information has to be maintained for a particular animal depending on the number of steps that it goes through. For example, if a carcass were subjected to twenty separate processes before it becomes a final product, each process would have to register that identification number. As each part of the animal goes to a different process, the information for each portion of the animal must be saved in the database as well. Again, this requires a large amount of data storage power and management of that system to ensure easy and accurate traceability of an end product back to its origin lot. Also, the proposed solution will not be available for quite some time and the implementation of such a system may be costly for producers and sellers alike.

Another problem with typical meat production processes is that the quality of an animal is typically assigned based on an analysis of the fifth ribeye. Depending upon certain characteristics of the ribeye, the animal will receive a grade. For instance, a high quality ribeye may result in the animal receiving a grade of prime, choice, or select based upon the amount of marbling, size, and sortation of the meat. There are many parts of an animal that may be better than other parts. For example, an animal may have a prime ribeye but the other portions of the animal may only be average at best. However, because the ribeye of the animal was scored as prime, the rest of the animal will receive the same score. This may lead to a misleading score of other portions of the animal. Alternatively, an animal that has a less than prime grade ribeye will receive less than prime ratings for the rest of the portions coming from that animal. There may be some portions of animals that have an equal quality, regardless of the grade of each animal's ribeye.

What is desired is an easy and effective animal and carcass tracking system that provides, among other things, for the quick traceability of an end product back to its origin.

SUMMARY

Methods and systems for tracking livestock during and after the production process are provided. Although well suited for use in bovine production, advantages offered by the present invention may be realized in the production of all types of animals including but not being limited to, bovine, porcine, and ovine animals as well as bison, poultry, and fish. Additionally, other production processes not related to animals may also benefit from embodiments of the present invention where tracking of inventory (e.g., other types of food or consumer products) throughout the production process is desired.

In accordance with one embodiment of the present invention, a system for managing and tracking a carcass is provided. In one embodiment, the system comprises a central processor that includes a tracking member, a database, and a meat production facility. The tracking member of the central processor is operable to receive information related to a carcass at one or more points in the production facility. Additionally, the tracking member is operable to determine a window of traceability during at least one of the fabrication process, the chilling process, the slaughter processes, and the preharvest process. The window of traceability may be based on ergonomic studies, rate of travel, quality assurance processes and any other available information that may lead to an amount of time required for a carcass or meat product to travel through the production process.

In accordance with another embodiment of the present invention, a method of tracing a meat product back to its origin is provided. The method comprises the steps of receiving a request for the origin of an end product, receiving and inputting label/identification information from the end product, determining a product fabrication time and/or fabrication window specific to that product, and determining the number of carcasses on the fabrication floor during that determined fabrication window. The method may further include determining carcass IDs for each determined carcass on the fabrication floor during that determined window and cross-referencing the carcass IDs to an animal. Once an animal or set of potential animals have been identified, the origins of animal lots may be determined and provided to a customer by generating a report.

The origin report may include information relating to a carcass identification number, a lot identification number, a kill date, fabrication time in hours, minutes and/or seconds including the date fabrication occurs, the number of potential carcasses (or portions thereof) in a box or cart, the number of potential animals (or portions thereof) in the box or cart that such carcasses were derived from, number of potential lots in the box or cart, and the animal feed lots of origin.

In accordance with another embodiment of the present invention, a device for tracing the origins of a meat product is provided. The device comprises an input for receiving at least end product information and a tracking member. The tracking member is operable to utilize the information received at the input and determine at least a potential production window of the identified carcass. The tracking member may also be further operable to determine a tracking window, a traceability window and may use the tracking window to determine the origin of an end product.

As used herein, an animal is a whole animal that has not been completely processed down to an end product. A carcass is at least a part of an animal, and therefore a number of carcasses may be associated with a single animal. A number of animals may be associated with a single lot. A lot of origin may correspond to a producer, feedlot, production lot, incoming lot, and so on.

One aspect of the present invention is to provide a system that can trace a product, either forwards or backwards, from a single point, throughout most, if not the entire, production (e.g. fabrication) process. This enables a questionable product to be recalled almost immediately before additional resources are expended to process a defective food product (e.g. a bad piece of meat). This also assists in quality assurance of the final products and thus higher customer satisfaction. By using embodiments of the present invention, a questionable piece of meat may be recalled/withdrawn from the production process within a time frame of about two hours, preferably in less than about 90 minutes, and most preferably within 50 minutes of detection.

Another aspect of the present invention is to provide improved sorting of carcasses throughout the production process. Improved sorting of carcasses, in turn, leads to subprimal maximizing. As can be appreciated, maximizing the tenderness of subprimal cuts of meat may lead to more consistent meat products, and improved customer satisfaction.

A further aspect of the present invention is to provide improved demand planning matched to carcass inventory. This can help to increase the efficiency of the production process and the entire supply chain because demand forecasting can help prepare downstream activities for increases and/or decreases in production before such increases and decreases occur.

Still another aspect of the present invention is to provide various producers and suppliers with valuable information that can be used for internal improvements or for sale back to suppliers. For example, as information is gathered and recorded for a particular animal, carcass, or subprimal portion of a carcass, that information may be used to improve supplies of future animals. Consider a supplier that has been paying a premium for high grade feed or paying for animal health supplies. If that supplier (or animal health product supplier) receives accurate information relating to results of the premiums that have been paid, then the supplier will be able to determine if the premiums paid are worthwhile. Additionally, the producer that is purchasing animals from the supplier will be able to more accurately determine what suppliers are supplying higher quality animals more consistently. All of these factors can lead to improved customer satisfaction.

Moreover, many companies focus on supplying dietary supplements, pharmaceuticals and the like, to animals before they are purchased. These companies usually claim that their product will help the animals be healthier and thus more valuable when they are purchased by a meat production facility. These types of companies may also be interested in receiving feedback related to various portions of the animals. For example, a company that supplies supplements aimed at reducing the number of organ abnormalities may be interested in knowing how many organ abnormalities were present in a particular lot that was treated with their product and how many organ abnormalities were present in another lot that did not receive their product. Many of these companies pay individuals non-trivial amounts of money to gather this sort of information. Using at least some embodiments of the present invention, a supplement and/or drug supplier can purchase information relating to certain portions of an animal that was treated with their product. This information can be, for example, gathered automatically and/or continuously and thus can be provided back to the supplier much more quickly and in more volume than could be realized in the past.

Yet another aspect of the present invention is to provide a system that is compliant with government regulations and can be easily updated and expanded to be in compliance with new government regulations. As new laws are passed that potentially restrict food, and particularly meat, production processes, it is important for producers to know that they can change as the rules change without requiring too many costs. Embodiments of the present invention provide for a relatively easily scalable and upgradeable system.

Still a further aspect of the present invention is to provide a system and method that can be used to accurately grade each subprimal portion of a carcass based upon the quality of that particular subprimal. Rather than grading an entire animal based on the ribeye section, each subprimal is analyzed and graded based on its own merit, not solely on the merit of the ribeye. This way the customer does not pay excessive prices for an over-graded product and the producer does not forego potential revenue for an under-graded product. Thus, one aspect of the present invention relates to obtaining and using at least two images of meat food products from one animal to determine the health and/or quality of such animal or food product. This helps to create more value for both the customer and the producer because each product (or at least two products deprived from any given animal) that is produced is given an accurate grade.

These and other advantages will be apparent from the disclosure of the invention(s) contained herein. The above-described embodiments and configurations are neither complete nor exhaustive. As will be appreciated, other embodiments of the invention are possible using, alone or in combination, one or more of the features set forth above or described in detail below.

BRIEF DESCRIPTION OF THE DRAWINGS

FIG. 5 is a conveyor belt for transporting parts of an animal through the production process in accordance with at least some embodiments of the present invention;

FIG. 6A shows a high grade organ in accordance with at least some embodiments of the present invention;

FIG. 6B shows a medium grade organ in accordance with at least some embodiments of the present invention;

FIG. 6C shows a lower grade organ in accordance with at least some embodiments of the present invention;

DETAILED DESCRIPTION

Figure 1:
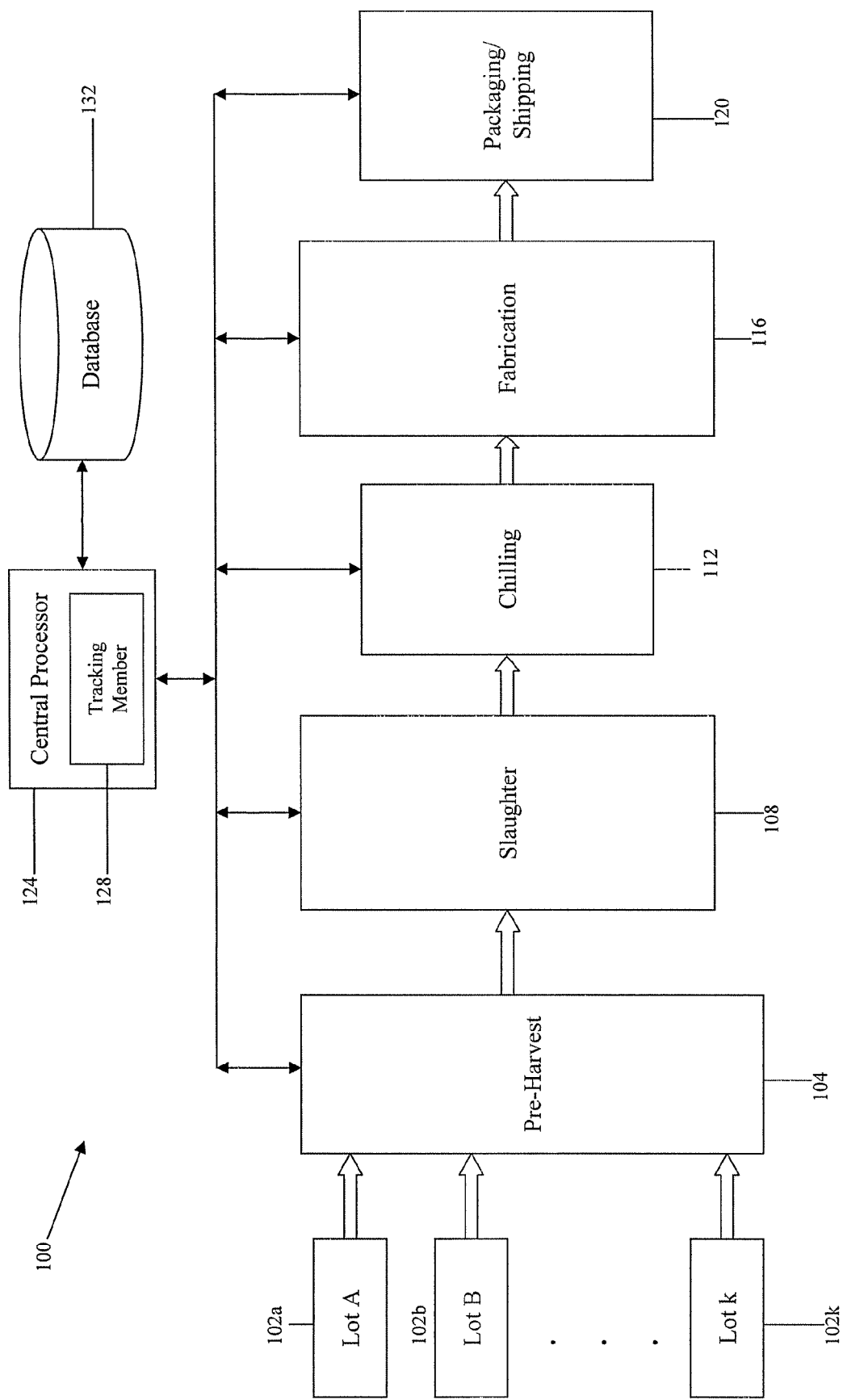
FIG. 1 is a block diagram of components of a meat production and tracking system in accordance with at least some embodiments of the present invention.

Referring initially to FIG. 1, a meat production and tracking system 100 will be described in accordance with embodiments of the present invention. The system 100, in the depicted embodiment, comprises a preharvest area 104, a slaughter area 108, a chilling area 112, a fabrication area 116, and a packaging/shipping area 120. The production system receives animals from lots 102A through 102k, where typically k≧1. Animals received from a given lot 102 go through the preharvest area 104 where they are associated with their supplier by way of the supplier's unique identifying number. A supplier number may be used to register that particular supplier with the meat producer and provides a convenient means for associating the lot number with the supplier number. Typically, a qualified supplier complies with Environmental Protection Agency (EPA) and Concentrated Animal Feeding Operations (CAFO) regulations.

Animals arriving at the preharvest area 104 from their respective lots 102 are assigned a lot number, corresponding to the lot which they were delivered with. Other information regarding the lot is also provided. For example, the number of animals in a particular lot 102, the sex of the animals in the lot 102, the feedlot of origin corresponding to the given lot 102, the day of slaughter, and other information may be recorded at the preharvest area 104. The production and tracking system 100 further comprises a central processor 124 comprising a tracking member 128 and a database 132. The determined information in the preharvest area 104 is sent to the central processor 124 via interface 136. The central processor then handles the information accordingly based on the required amount of information needed at any given step along the production process, and stores that information in a suitable format in database 132. The interface 136 may be a bidirectional interface allowing communications to/from the central processor 124 and various components of the meat production system 100. Alternatively, the interface 136 may be a unidirectional interface that simply transfers information from any one of given areas to the central processor 124.

In production, the animals are taken from the preharvest area 104 to the slaughter area 108 where they are slaughtered. In the slaughter area 108, the hide of the animal is removed from the carcass and the carcass in washed. The carcass may also be steamed pasteurized, receive a euhygenic bacteria treatment, and/or be subjected to an electrical stimulation process. In the slaughter area 108, carcasses are cross-referenced with animal ear tags otherwise known as a head tag system, which maps every carcass to an individual animal. Ear tag and head tag are paired, collected, and recorded at the slaughter area 108. The information that is recorded in the slaughter area 108 is again sent to the central processor 124 where it is accordingly processed and then saved in database 132 in the appropriate format.

Also in the slaughter area 108, a carcass crosses a scale where the carcass is weighed and assigned a unique carcass identification number. The carcass identification number references the animal number and the corresponding lot number. The unique carcass identification number may also contain additional data including the kill date, the processing shift, and the hot carcass weight per side. Typically an animal is split into two sides therefore having two carcasses correspond to a single animal. As noted above, this unique carcass identification number is also sent from the slaughter area 108 to the central processor 124 for storage in the database 132.

After the animal has passed through the slaughter area 108, the corresponding carcasses are sent into the chilling area 112 where they are suitably chilled for a predetermined amount of time. After a carcass has been chilled for the requisite amount of time, it is sent into the fabrication area 116, where it is again weighed. The weight is logged at the transfer scale between the chilling area 112 and the fabrication area 116 and the chilled carcass weight typically per side is recorded and sent to the central processor 124. Additional information including, but not limited to, time of processing, shift that the carcass was processed at the transfer scale, animal identification number, and corresponding lot number may be saved and sent to central processor 124 for storage in the database 132 as well.

In the fabrication area 116 the carcass is separated into different parts. For example, one beef carcass may be split into a butt section, a chuck roll section, a strip section, a top round section, a bone-in-rib product, or any other suitable meat product that can be derived from the carcass. Each product class has a processing time associated with it. Quality assurance, ergonomic studies, time and travel across fabrication floor, and any other information that can be used to determine the amount of time it takes for a carcass to travel through the fabrication area 116. This processing time typically corresponds to a window of traceability 300, as will be described in further detail later. Each window of traceability 300 can be traced to a carcass identification number, lot number, and feed lot of origin. This window of traceability 300 may be saved in the database by transferring the information from the fabrication area 116 to the central processor 124 where it is saved in the database 132, though this is not required as it is commonly known how long a particular product takes to be produced in the given fabrication process.

Once the carcass has been properly processed into a final product, it is sent from the fabrication area to the packaging and shipping area 120 where it is packaged and boxed, and each box is labeled with information. The box information may include product code corresponding to the type of product that is within the box, product serial number, time of production, production shift, and/or destination. The final boxed or packaged product is then sent from the packaging and shipping area 120 to either a retailer or an end customer.

Figure 2:
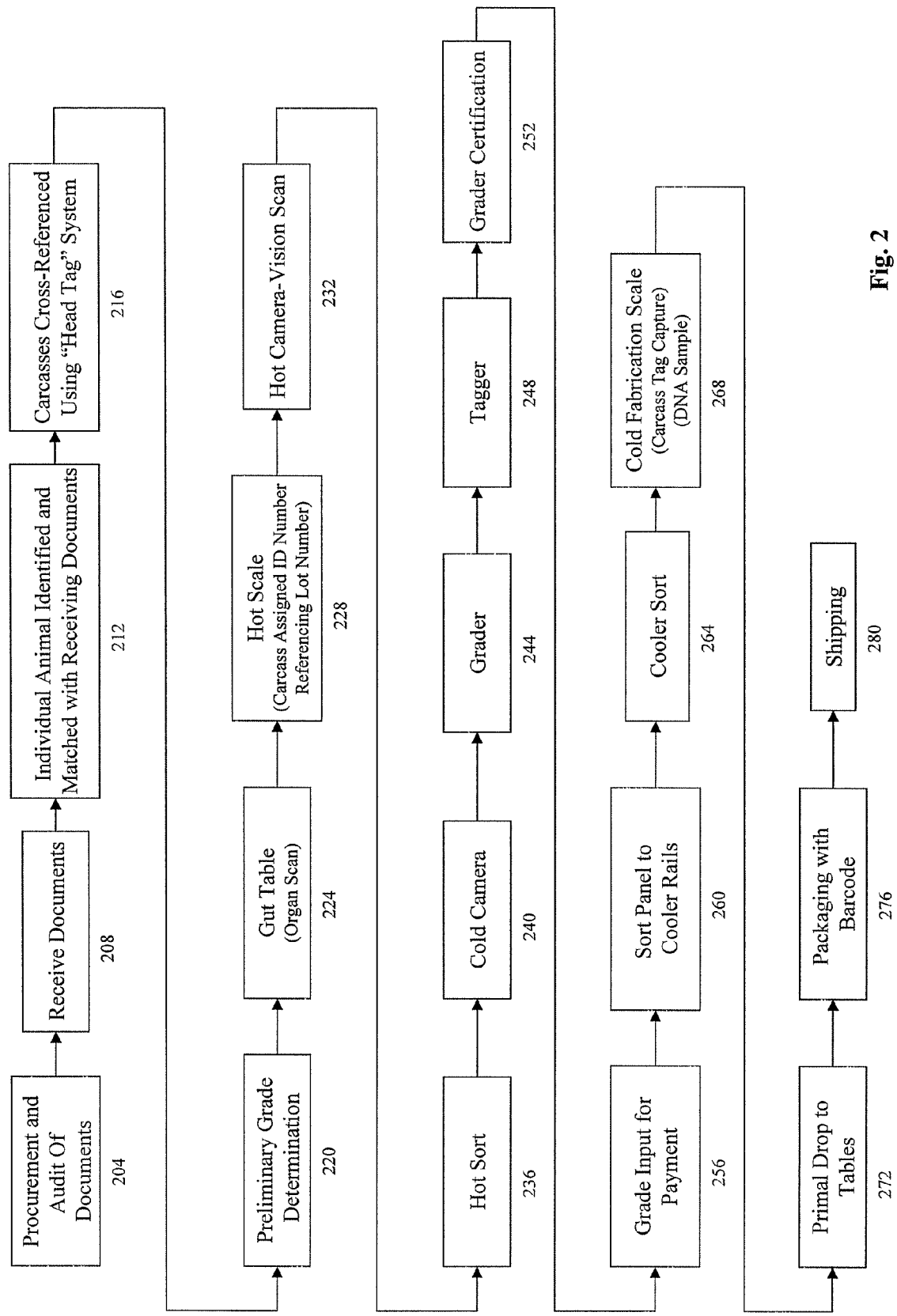
FIG. 2 is a block diagram depicting a general production and tracking process in accordance with at least some embodiments of the present invention.

Referring now to FIG. 2, a more detailed description of the production and tracking process will be described in accordance with embodiments of the present invention. In step 204, documents relating to a lot and/or animal associated with a particular lot are procured. In this regard, but not portending to be limited in any manner, the following U.S. Patents are incorporated herein by reference to assist in providing a written description of how one of skill in the art may implement one or more embodiments of the present invention: U.S. Pat. No. 5,478,990 to Montanari et al. and U.S. Pat. No. 6,975,223 to Grose et al. Procurement and audit of documents may include vision supply base, future supply projections, information supplier's data, and other relevant supplier information. Thereafter, the documents are received at the preharvest area 104. The received documents are generally used to verify the age of incoming animals and the source of these animals. Certification may also include determining whether the animals are organic and natural (i.e., have not been exposed to chemicals or other additives) (step 208). In step 212 each individual animal is identified and matched with receiving documents. For example, if fifty animals were received in a particular lot 102, then each animal is matched to that particular lot 102. The animal records are gathered if necessary and the animal identification number is recorded and sent to central processor 124. The animal may also undergo an optibrand vision scan and the receiving documents of the lot matched to that animal. Thereafter, the animal is sent from the preharvest area 104 to the slaughter area 108 as described above.

In the slaughter area 108 the carcass is cross-referenced using a head tag system linking the individual animals identification number to the lot number (step 216). Thereafter, an Angus determination is made and if applicable, the carcass is stamped with an "A" as having a high grade of meat (step 220). In step 224, the carcass is sent to the gut table where a loss report is generated to determine how healthy the animal was. If, during the viscera test, it is determined that the animal's health is questionable, then all carcasses associated with that animal are recalled and tested further to ensure the quality of the meat.

At the gut table, an additional step may be performed where the organs of the given carcass are scanned. When the organs are removed from the carcass, they are typically placed on a conveyor belt or the like. As can be seen in FIG. 5 the conveyor belt 500 is generally divided into a first and second section 504 and 508 respectively. Organs on the belt 500 are generally separated such that an organ of interest 512 is placed on the first section 504 and the other viscera 516 are placed on the second section 508. Examples of the organ of interest 512 may include all commercially useful internal organs derived from an animal, including, but not limited to, brain, liver, tongue, pancreas gland, thymus gland, stomach, feet, kidney, lungs, heart, small intestine, testicles, placenta, crop and/or caul. The organ is placed onto the first section 504 of the belt 500 and travels in the general direction of arrow 518. As the organ moves with the belt it is passed under an optical instrument capable of generating an image of the organ 520, such as still images or sequences of moving images. This image generation means 520 is arranged such that an image is generated of any organ that passes through an area of interest 522 underneath the image generation means 520, and may be equipped with a motion detector or the like that helps to automatically detect the presence of an organ in the area of interest 522. The image gathering means 520 may be one of many items capable of creating an image, photographic or otherwise, of the organ as it passes underneath, such as a camera (film or digital; color or black and white), a video camera (film or digital; color or black and white), an Internet-operable web camera, an x-ray device, colorimeter, fiberscope, optrode, infrared sensor (passive or otherwise), photodetector, photometer, telescope, videoscope, and/or any similar device as well as any combination of the foregoing. In the presently preferred embodiment, the image gathering means 520 is a camera, more preferably a digital color camera. An image generated by such a device may be of any form capable of being transmitted electronically to the processor 124, such as an electronic image or a paper image that is capable of being converted to an electronic image, such as by scanning or similar means known to those of skill in the art.

Once the organ is within the area of interest 522 the image gathering means 520 captures an image of the organ, which is then sent to the processor 124. The processor 124 determines what animal and/or lot the organ is associated with and creates a pointer between the subject image of the organ and the animal/lot that the organ is associated with. The pointer may be a memory address of the data for the animal/lot. The processor 124 may alternatively stamp the image with the corresponding animal/lot identification number/name such that anyone that looks at the image knows what animal the organ came from and subsequently what lot the animal originated from. The processor 124 then sends the image to the database 132 for storage.

Referring now to FIGS. 6A-C exemplary images captured by the optical device 520 will be discussed in accordance with at least some embodiments of the present invention. The organ shown in FIG. 6A has no visible abnormalities and appears to be healthy; as such, it has been given one stamp 604 as an indication that the organ is healthy. Typically, in the United States, a USDA employee stands at the belt 500 and grades each organ that may be consumed by humans and/or animals. The grader is responsible for assigning each organ a grade based on its merits. Since the organ shown in FIG. 6A appeared to be healthy, it was given one stamp that generally signifies a healthy organ. When the processor 124 receives the image of FIG. 6A, the processor 124 may use image processing techniques to determine that the organ was given only one stamp.

The image shown in FIG. 6B has a few abnormalities 608 (i.e., abscesses) and thus has been given different grade from the organ in FIG. 6A. Namely the organ in FIG. 6B has been given two stamps 604 indicating that the organ is safe for animal consumption but not for human consumption. The few abnormalities may be an indication to either the rancher responsible for supplying the animal or a company that supplied supplements to the rancher that something is wrong with either the animal or the animal's diet.

The image of the organ shown in FIG. 6C has a number of abnormalities 608 and as a result has been given a much lesser grade than the previously discussed organs. It has thus been given three stamps 604 indicating that the organ is not safe for human or animal consumption as is, and therefore must be removed from production and destroyed.

There are a number of ways to indicate the grade that a particular organ has received. As discussed above one scheme for indicating the grade of a particular organ corresponds to how many stamps the organ receives. The more stamps the organ has received, the lesser the quality of the organ. As can be appreciated by one of skill in the art, multiple stamps may indicate that the organ has a higher quality than another organ that has fewer stamps.

As noted above, the images of the organs are sent to the central processor 124 where they are analyzed. Typically the processor 124 searches for and counts the number of stamps 604 that appear in the image and registers the grade of the organ 512 based on the number of stamps 604 that it observes. Alternatively, the processor 124 may not rely on stamps 604 and could instead count the number of abnormalities 608 that exist on the organ 512. Using certain image processing techniques the darker values of the pixels associated with abnormalities could be counted and if the number of abnormally valued pixels (e.g., pixels that have a darker color than their surrounding pixels) exceeds a certain threshold, then the quality of the organ can be downgraded. In order to identify abnormalities and/or the stamps applied by the grader, the processor 124 is operable to scan the image and determine the value of each pixel. Typically, a darker pixel is given a higher intensity value and a lighter pixel is given a lower intensity score. The processor 124 compares the intensity values of each pixel and those immediately next to the pixel. When the processor 124 identifies a pixel that has one or more pixels next to it with a substantially different intensity value, then the processor 124 marks that pixel as a potential abnormality and/or stamp. The processor 124 then tries to determine if a number of marked pixels are in a group. If there are a number of marked pixels in a group, then the processor 124 can mark the group as a potential abnormality and/or stamp. The size and shape of the group is analyzed to further determine whether the group is an abnormality or a stamp. The number of abnormalities or stamps are then counted to determine what grade the organ was given or what grade it should be given. Once the processor 124 determines the grade then the grade is associated with the lot and/or animal that the organ originated from. This valuable information may be stored in the database 132 and sent to the supplier of the lot for analysis of the quality of the lot.

Again each organ is associated with an animal and therefore one or more carcasses. During the organ scan an image gathering means 520, which is preferably a digital color camera, is used to scan each organ as it passes over the gut table. By scanning the organ with an image gathering means 520, abnormalities may be identified be analyzing the image obtained. If abnormalities are discovered, the carcass(es) associated with that organ could be recalled immediately prior to any additional production on that meat. A higher number of organ abnormalities may indicate that the animal was not a healthy animal and therefore may not be able to meet suitable quality standards set forth. If, during organ scanning, it is determined that the animal was unhealthy, the carcasses associated with that organ are recalled and further quality testing is performed to ensure that the carcasses are suitable for consumption.

Figure 7:
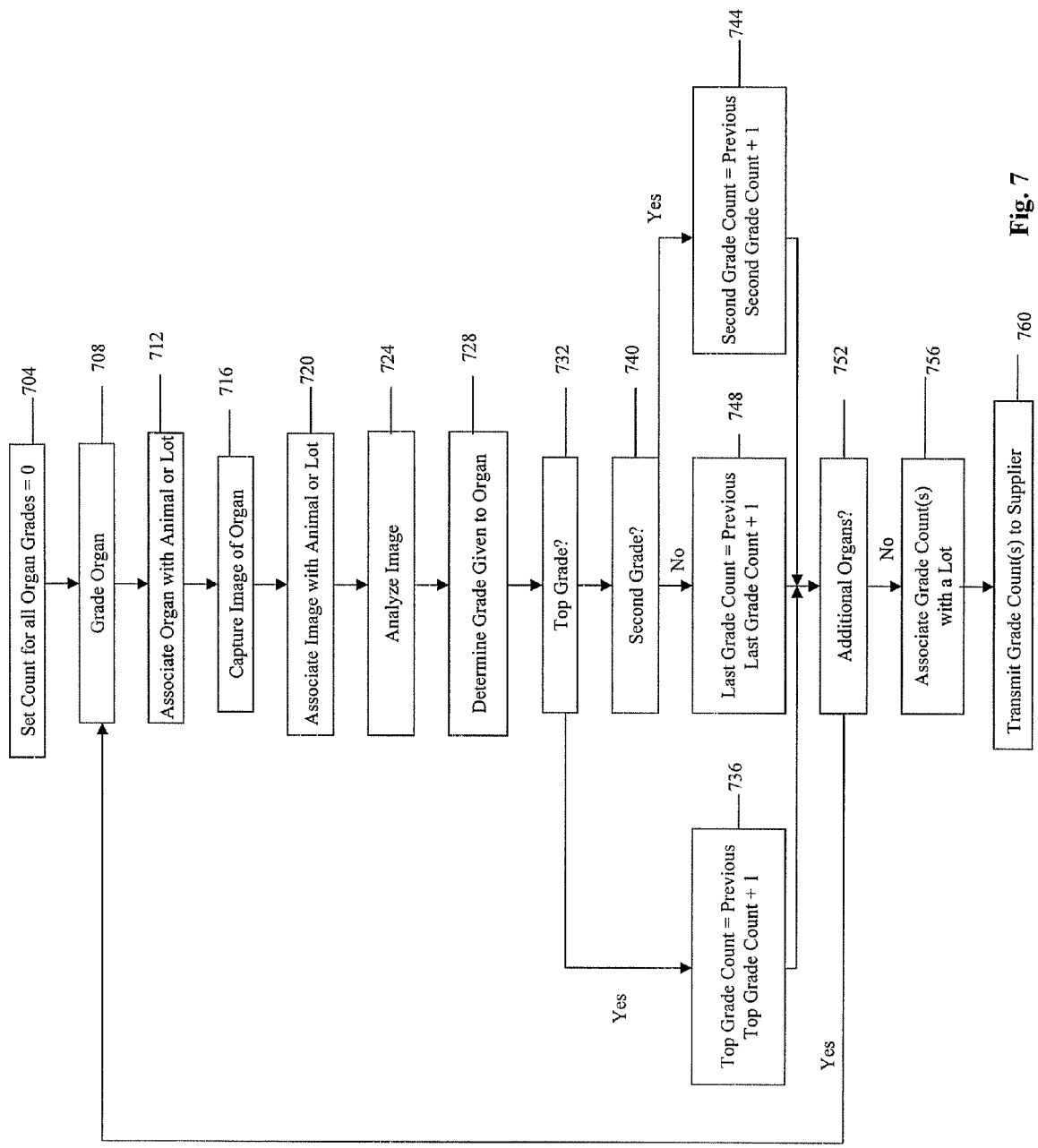
FIG. 7 depicts a method of tracking and accounting organ quality in accordance with at least some embodiments of the present invention.

Referring to FIG. 7 a method of scanning organs of interest 512 during meat production will be described in accordance with at least some embodiments of the present invention. Initially, a count variable for all of the organ grades is set to zero (step 704). Thereafter, a first organ is graded by either manual or automatic methods (step 708). The graded organ is then associated with an animal/lot (step 712). By associating an organ with an animal and/or lot, information already stored in the database 132 regarding that animal/lot can be logically connected with the organ such that any additional information that is determined about the organ can also be stored with the animal/lot information in the database 132.

As the organ 512 passes into the area of interest, an image of the organ 512 is captured by an image gathering means 520 (step 716). The image is transmitted to the processor 124 and associated (e.g., stored in the database with images of other organs from the same animal/lot or stamped with animal/lot information) with an animal/lot (step 720). Then in step 724 the processor 124 analyzes the image to determine how many, and possibly what kind of, markings, abnormalities, and/or stamps exist on the organ 512(step 724). Based on this analysis, the grade of the organ 512 is determined by processor 124 and stored with the rest of the pertinent information relating to image and/or the animal/lot associated with the image.

In step 732, it is determined whether the organ 512 was given the top grade. In the event that the organ 512 has received a top grade, then the variable corresponding to the top grade count for a given lot is incremented by one from its previous value, which would be zero for the first organ (step 736). However, if the organ 512 was not given the top grade then it is determined if the organ 512 was given the second highest grade (step 740). If the organ 512 was given the second highest grade, then the variable corresponding to the second highest grade count is incremented by one from its previous value (step 744). If the organ was not given the second highest grade then the lowest grade count is incremented by one from its previous value (step 748). For purposes of illustration only three grades have been described, but it is possible to implement embodiments of the present invention where numerous grades exist for a particular meat product. Each grade would have a corresponding variable dedicated to keeping track of the number of organs that have received that grade. Once the variable associated with the grade of the organ has been incremented, it is determined if there are any additional organs that need to be analyzed (step 752). If there are more organs that have to be scanned, then the method returns to step 708.

Once a suitable number of organs have been analyzed (e.g., all of the organs from animals corresponding to a particular lot), then the grade counts of each variable are associated with a lot (step 756). In a preferred embodiment, when an organ associated with a new lot is scanned, then the value for each variable of each grade count is stored with other lot information and the variables are reset to begin counting for the new lot. After a suitable number of organs have been scanned and the grade counts of the scanned organs are stored along with the other lot information, the grade counts and any other pertinent information is forwarded to the supplier of the lot (step 760). This provides easily verifiable and accurate feedback to the lot supplier about the quality of his/her lot. Additionally, the information can be sent to other suppliers. For example, organ information may be transmitted to a company that supplies ranchers with medicine that is supposed to decrease the number of organ abnormalities. If the number of low quality organs is substantially lower than other lots that did not use the medicine supplied, then the company supplying the medicine can have additional proof of their product's efficacy and can therefore attempt to charge a premium for their medicine. As can be appreciated, the information from scanning organs of interest 512 may be valuable to a number of other entities involved in the meat production supply chain.

Figure 8:
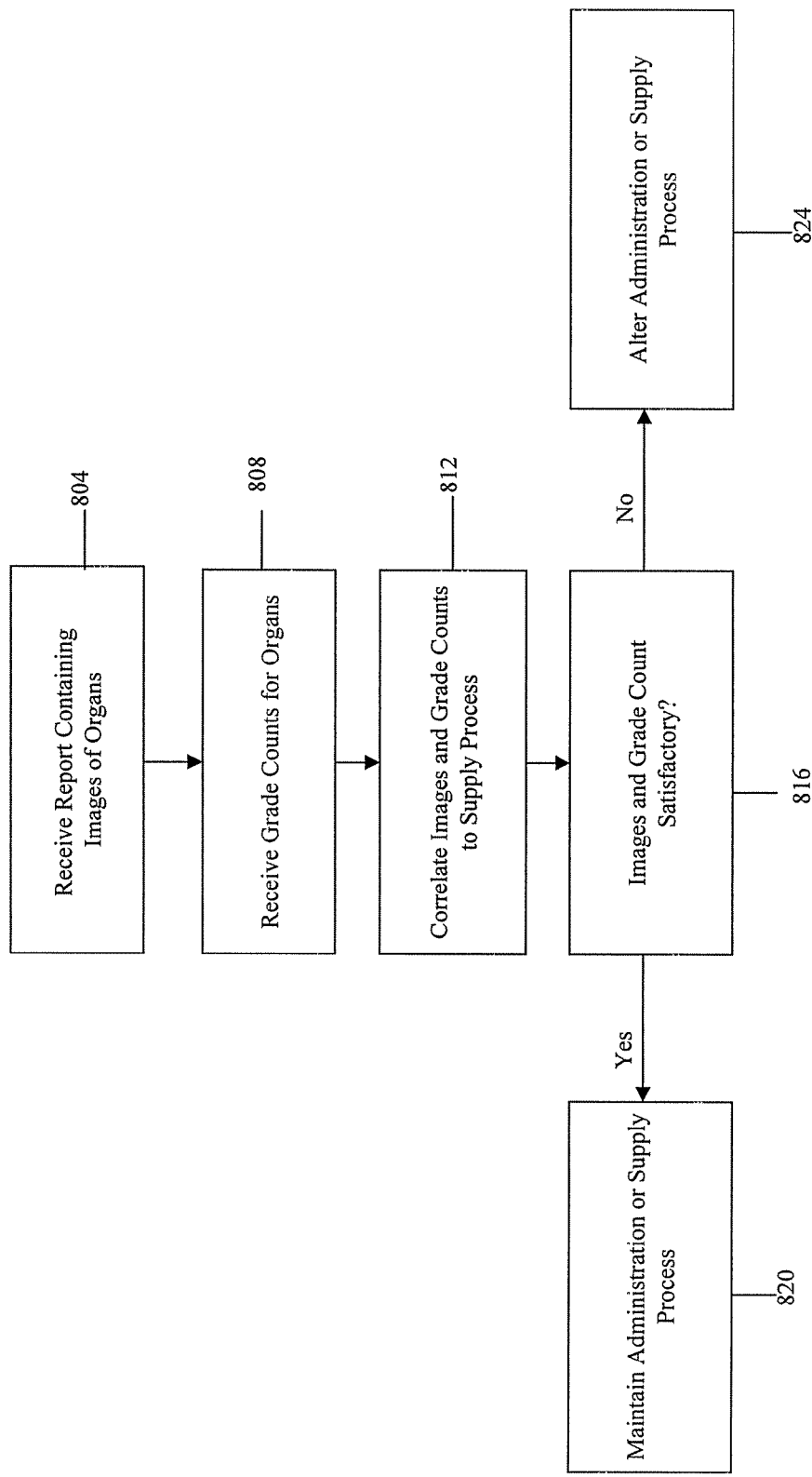
FIG. 8 depicts a method of utilizing accounting information in accordance with at least some embodiments of the present invention.

Referring now to FIG. 8 a method of utilizing information supplied from the organ scanning method will be described in accordance with at least some embodiments of the present invention. Initially, images of the organs and other information related to the lot (e.g. number of animals in the lot, overall quality of the lot, price paid for the lot, price paid per head of animal, time of day lot was processed, lot number, and so on) are transmitted to the supplier (step 804). The images of the organs may include a written description of the grade of the organ along with the associated lot number and corresponding animal number. The supplier also receives the grade counts for the organs, typically along with the images of the organs (step 808). The grade counts may correspond to the member of organs that had a particular grade score. For example, a given lot may have had a large number of organs with a top quality grade, a moderate number of organs with a second quality grade, and a small number of organs with the lowest quality grade. The images may be correlated to the grade counts in order to verify the accuracy of the grade counts (step 812).

Based on the feedback received by both the images and the grade count for each image, the supplier can determine how best to proceed with raising animals. In step 816, it is determined if the images and grade count correspond to a satisfactory level. For instance, if the number of lowest quality grades received is larger than a predetermined percentage of the entire lot, then the lot may not have been raised to a satisfactory level. In the event that the lot did meet the minimum requirements, then the supplier may decide to maintain his/her process (step 820). However, if the feedback shows that the supplier is raising lower quality animals then the supplier may decide to alter the process they use to raise their cattle. For example, if the supplier had not previously been purchasing medicine for maintaining healthy animals, then the supplier may choose to begin purchasing medicine that helps improve his/her animals' health. Additionally, the information can be provided directly to the pharmaceutical supplier so that they can determine if their product is working effectively. If the product is working effectively, then the pharmaceutical supplier may be able to ask a premium for their product. Conversely, if the feedback indicates that their product does not work, then the pharmaceutical supplier may need to redesign their particular product.

After the organ has been scanned and other necessary tests have been performed, the carcass is sent to a hot scale (step 228). At the hot scale, each carcass is given a unique identification number linked to the head tag. This references the lot number, contains additional data including the kill date processing shift, hot carcass weight per side and so on. That information is then transferred to the central processor 124 for storage in database 132. Thereafter, in step 232, each carcass is analyzed with another means for gathering an image, such as a hot camera, that enables the user to make an initial determination or prediction of the meat's quality. Examples of what can be determined by utilizing this image gathering means include, but are not limited to, a confirmation score, a muscularity index, primal measurement, prediction of subsequent primal measurements, and correlation with subprimal. Thereafter the carcass is sent to the hot sort in step 236.

Once the slaughter process has been completed the carcass is sent into the chilling area 112 where initially a third image gathering means, such as a cold camera, is used to determine the vision, the rib-eye size, color, fat cover and marbling of each carcass (step 240). This information is used by a grader to determine yield grade, quality grade and so on (step 244). Thereafter, the tagger tags the carcass and captures data related to that carcass. That data may include data that was recovered from the cold camera, the grader or any other previously performed step. The information is then sent to the central processor 124 for storage in the database 132.

In step 252, a grader certification is performed meaning that the original grade is confirmed by a second party. In step 256, grade input for payment is performed. This typically involves determining the actual amount of money that may be received for the given grade. The carcass is then sent to a sort panel to be stored on cooler rails in step 260. Thereafter, the carcass is sorted and stored for a predetermined amount of time in step 264. During cooler sort, the location of the carcass is known and may be tied to any of the previously mentioned information. This enables the production facility to quickly locate the carcass in the cooler if it is determined that the given carcass needs to be recalled and/or retrieved for any purpose.

After the carcass has stayed in the cooler for a predetermined amount of time, the carcass is sent from the chilling area 112 to the fabrication area 116. As the carcass passes between the chilling area 112 and the fabrication area 116, it is weighed at a cold fabrication scale. Again at the cold fabrication scale, the carcass tag information is captured and stored and sent to the central processor 124 and stored in the database 132. Additionally, a DNA sample may be taken from the carcass as it passes across the cold fabrication scale. This may ensure a higher level of accuracy in determining and tracing the origins of a carcass. Thereafter, a primal drop of two tables is performed in step 272. Each product may be sorted and produced according to known methods.

Figure 3:
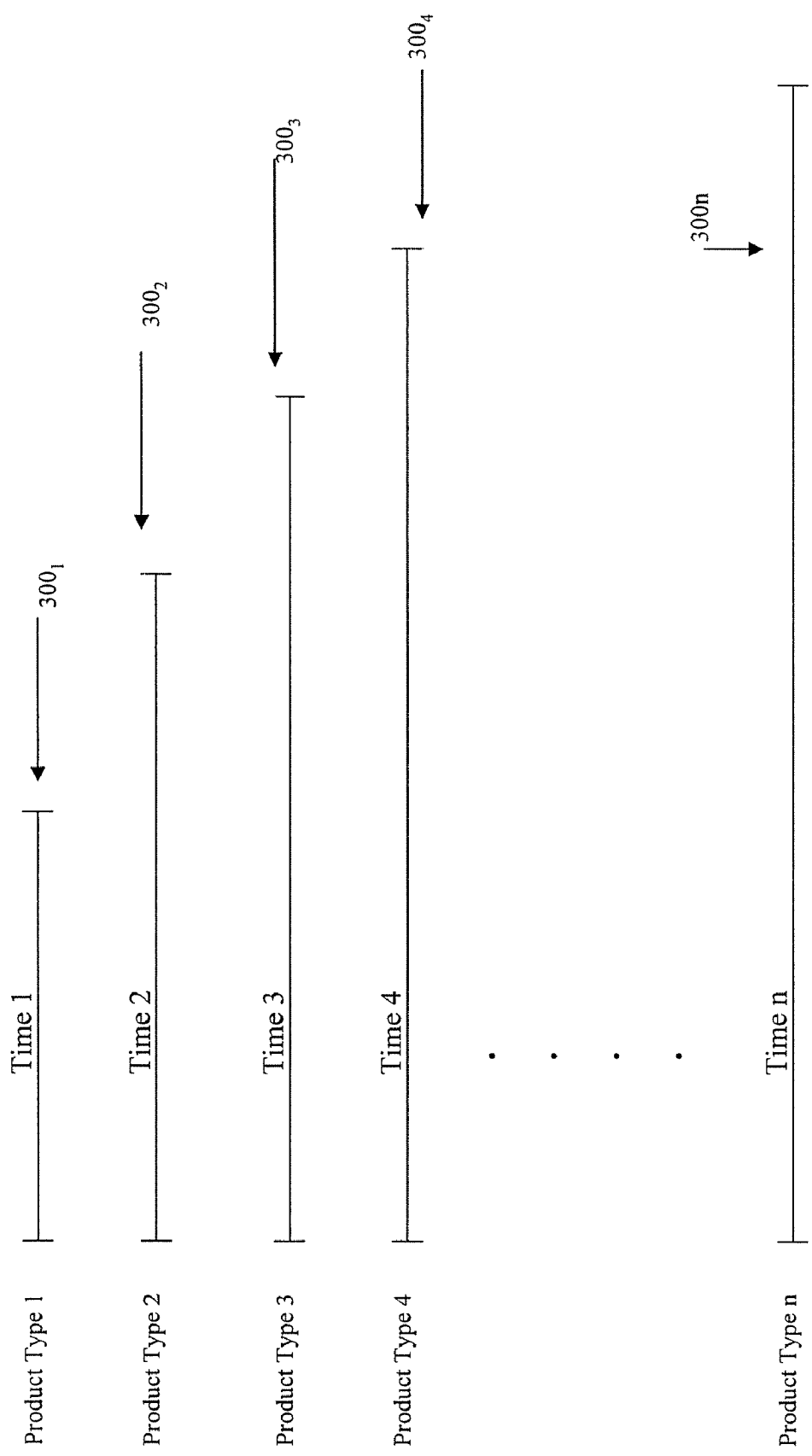
FIG. 3 is a depiction of various processing time windows of traceability in accordance with at least some embodiments of the present invention.

Referring now to FIG. 3, an explanation of the different types of products and the amount of time required to produce such products will be discussed in accordance with embodiments of the present invention. Because the fabrication process is a known process, it is possible to create a window of traceability 300 that allows each product to be accurately traced though the fabrication process. For example, a top butt of a beef carcass may correlate to product type 1. Time 1 may take about 17 minutes to produce that particular type of product. This results in a first window of traceability $300_1$ approximately equaling 17 minutes for the first product. A second product such as a beef strip loin may take a longer amount of time to produce. Based on ergonomic studies and known fabrication methods it may be determined that the second window of traceability $300_2$ is approximately 18.5 minutes for the strip loin. Again, each window of traceability 300 may correspond to a different product. Each time a window of traceability 300 is determined, it can be traced to a carcass' ID, lot number, and ultimately feedlot of origin. There may be up to n types of products in a given fabrication process, where typically $n \geq 1$. Each of these products may have a different (though not necessarily required to be different), window of traceability 300.

Referring back to FIG. 2, once each product has been produced, the product is sent to the packaging and shipping area 120 where it is packaged with a packaging bar code. Packaging may include individually packaging each product or grouping a number of products together into a box, for example, such that the box contains a number of carcasses. One box may correspond to four or five different carcasses and each carcass is not necessarily associated with the same animal. However, the information printed on the box may include the product code or the type of products that are packaged within, serial number of the box, time of packaging of the box and the production shift in which it was packaged. Again this information is sent to the central processor 124 and saved in the database 132. Once the packages have been properly labeled in step 276, they are shipped to the end customer in step 280.

Figure 4:
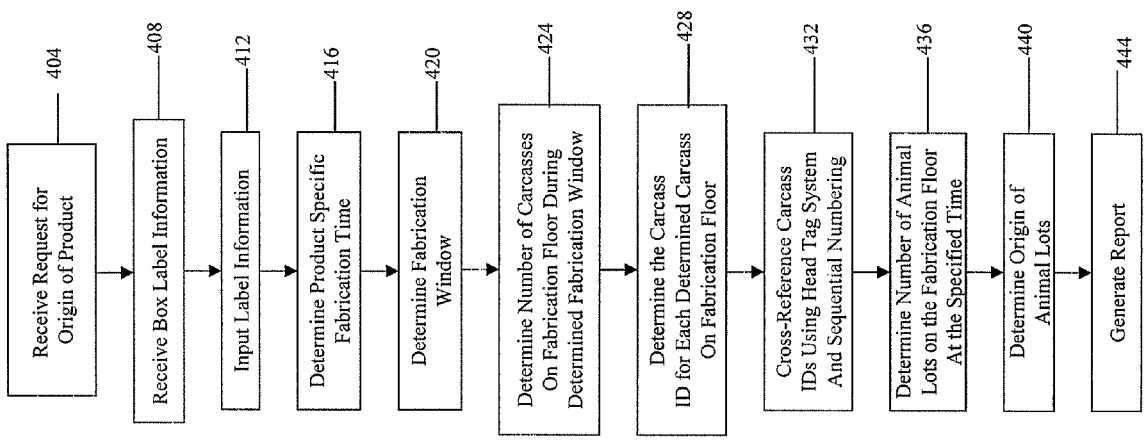
FIG. 4 shows a method of determining the origin of end products in accordance with at least some embodiments of the present invention.

Referring now to FIG. 4, a method of tracing back the origin of an end product will be described in accordance with embodiments of the present invention. Initially, in step 404, a request for an origin of a product is received at the tracking member 128. The request preferably includes box label information, which is received by the meat producer in step 408. Suitable box information may include box serial number, the product code, time of production/packaging of the box, and the production shift in which the product was packaged. Upon receipt of the requisite box label information in step 408 the box label information is input into the tracking member 128 in step 412. The box label information may be input directly to the central processor 124 or may be input at a remote terminal that can communicate with the central processor 124 and/or the database 132.

Once the label information is input, the product specific fabrication time is determined in step 416. Using the product specific fabrication time, a corresponding 10 fabrication window or window of traceability 300 is determined in step 420. The window of traceability 300 may be used to help determine the number of carcasses that were on the fabrication floor during the determined fabrication window (step 424).

Once the number of carcasses on the fabrication floor during a given window of traceability 300 is determined, the tracking member 128 may be able to determine the carcass ID for each determined carcass on the fabrication floor in step 428 utilizing information from the database 132. The tracking member 128 may then cross-reference the carcass IDs using the head tag system. The cross-referencing performed by the tracking member 128 in step 432 then allows the number of animal lots to be determined in step 436. Specifically, the tracking member 128 determines the member of animal lots on the fabrication floor during the determined window of traceability 300. That information can then be used to determine the origin of each of those animal lots in step 440. Based on this information, the tracking member 128 may then be able to generate a report for the requester of the origin information. The report may include, but is not limited to, the carcass ID, lot identification number, kill date, fabrication time, number of potential carcasses in the box, number of potential animals in the box, potential number of kill lots in the box, and the corresponding animal feed lot of each kill lot. This information is generally based on the window of traceability 300 and the corresponding information that was stored in the database 132.

This management and tracking system 100 allows for backwards and forwards tracking of a carcass/animal from any point during the production, fabrication and consumption process. Any carcass or animal may be recalled or withdrawn within a time frame of about two hours during the production process.

The data management and tracking system may also be used to produce reports and sell data back to producers by lot and/or by individual animals within that lot. Also various steps, for example, the organ-scanning step, may be correlated with other steps and information related to that test is maintained in the database 132 along with the corresponding carcass/animal. That data may be sold back to animal health suppliers to allow them to determine how certain animals and/or lots are affected by a particular type of treatment for organs and/or any other health concerns.

The system is also compliant with USDA and FDA regulations therefore making it safe and reliable to the consumers. The process may also improve sortation of the carcass which in turn leads to subprimal maximization. Additionally, because the window of traceability 300 can be determined throughout the production process, information relating to the fabrication of a given product type does not necessarily need to be stored in the database 132 for each carcass. This makes it easier to maintain a database 132 and track carcasses during the fabrication and production process.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of tracing the origins of a product, comprising:
   receiving a request for the origin of the product, wherein the request comprises information about the product;
   based on the information received about the product, determining a corresponding window of traceability for the product;
   determining at least one carcass that was present at a production facility during the window of traceability;
   determining a lot associated with the at least one carcass;
   reviewing an image of an organ separated from said at least one carcass; and establishing, based on a computer analysis of said image, whether said at least one carcass was administered a drug during its life span.

2. The method of claim 1, further comprising generating a report containing information regarding the origins of the product.

3. The method of claim 1, wherein the product is a meat product.

4. The method of claim 1, wherein the product is an organ.

5. The method of claim 4, wherein the organ is selected from the group consisting of brain, liver, tongue, pancreas gland, thymus gland, stomach, feet, kidney, lungs, heart, small intestine, testicles, placenta, crop and caul.

6. The method of claim 1, wherein the production facility is a meat production facility.

7. A system for producing and tracking a meat product, comprising:
   a meat production facility comprising a number of production areas;
   means for capturing images of animal organs that pass within an area of interest in at least one production area;
   a database used to store information relating to the images and products that are produced within the meat production facility; and
   a central processor that is operable to receive information relating to the images and products from at least one of the production areas and transfer the information to the database for storage, wherein the information at least comprises a window of traceability corresponding to at least one of the production areas.

8. The system of claim 7, wherein the means for capturing images is a camera.

9. The system of claim 8, wherein the camera is a digital camera.

10. The system of claim 7, further comprising means for generating a report containing information regarding the origins of the meat product.

11. A method for auditing a meat production process, comprising:
    separating at least one organ of interest from other organs;
    grading the at least one organ of interest;
    capturing an image of the at least one organ of interest;
    associating the at least one organ of interest and the image with at least one of an animal and a lot of origin;
    analyzing the image using a computer;
    based on the analyzing, determining the grade of the at least one organ of interest; and
    associating the determined grade of the at least one organ of interest with the at least one of an animal and lot of origin.

12. The method of claim 11, wherein the organ is selected from the group consisting of brain, liver, tongue, pancreas gland, thymus gland, stomach, feet, kidney, lungs, heart, small intestine, testicles, placenta, crop and caul.

13. The method of claim 11, further comprising generating a report containing information regarding the organ's animal of origin.

14. The method of claim 11, further comprising generating a report containing information regarding the organ's lot of origin.

* * * * *